United States Patent [19]

Koletar et al.

[11] 4,272,539
[45] Jun. 9, 1981

[54] PYRIDOINDOLE DERIVATIVES

[75] Inventors: Gabor I. Koletar, Berkeley Heights, N.J.; Jonathan R. Frost, Palaiseau, France; Regis Dupont, Paris, France; Patrick Lardenois, Bourg la Reine, France; Claude Morel, Massy, France; Henry Najer, Paris, France

[73] Assignee: Synthelabo, Paris, France

[21] Appl. No.: 112,212

[22] Filed: Jan. 15, 1980

[30] Foreign Application Priority Data

Apr. 26, 1979 [FR] France ................................ 79 10654

[51] Int. Cl.³ ................. C07D 471/04; A61K 31/435
[52] U.S. Cl. ..................................... 424/256; 546/85; 546/86
[58] Field of Search ..................... 546/85, 86; 424/256

[56] References Cited

U.S. PATENT DOCUMENTS 4,091,102  5/1978  Teller ..................................... 546/85

Primary Examiner—Alan L. Rotman
Attorney, Agent, or Firm—Wegner & Bretschneider

[57] ABSTRACT

Pyridoindole derivatives of formula

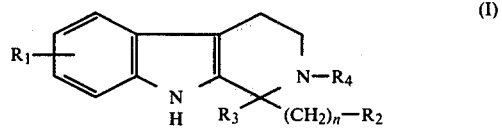

(I)

$n=0$ or 1; $R_1=H$, Hal, alk, alk-O-, $CF_3$; $R_2=$—COOalk; —CONHR$_5$ ($R_5=H$ or various substituents); $R_3=H$, alk, —COOalk; $R_4=H$, Ac, alk, —CONHR$_6$ ($R_6=H$ or various substituents), and acid addition salts, except certain known compounds, are useful in treating anoxia and depression and in psychotropic therapy. They are prepared from tryptamine or a derivative thereof by reaction thereof with a pyruvic ester or 3-ethoxycarbonyl-1,2-dioxo-1-ethoxypropane to form compounds in which $R_4$ is H and $R_2$ is —COOalk. These compounds are reacted with amines, isocyanates or usual N-acylating or N-alkylating reagents to prepare the other compounds.

4 Claims, No Drawings

PYRIDOINDOLE DERIVATIVES

DESCRIPTION

This invention relates to pyridoindole derivatives useful in therapy.

The pyridoindole derivatives provided by this invention are in the form of racemates or optically active isomers, and are compounds of the formula

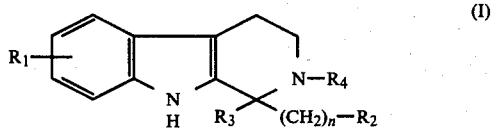
(I)

in which n is 0 or 1, $R_1$ represents a hydrogen or halogen atom, an alkyl or alkoxy radical or the group $CF_3$, $R_2$ represents either an alkoxycarbonyl radical or a radical $CONHR_5$, in which $R_5$ is an alkyl, cycloalkyl or benzyl radical, a phenyl radical which can carry a substituent, or a hydrogen atom, $R_3$ is a hydrogen atom, an alkyl radical or an alkoxycarbonyl radical and $R_4$ is either a hydrogen atom or an acyl radical or an alkyl radical or a radical $CONHR_6$, in which $R_6$ is a hydrogen atom or an alkyl, cycloalkyl, benzyl, phenyl or substituted phenyl radical, the alkyl and alkoxy radicals having from 1 to 4 carbon atoms and the cycloalkyl radicals having from 3 to 6 carbon atoms, with the exception of the compounds wherein simultaneously n=0, $R_1$=H, $R_2$=COO(Et or Me), $R_3$=H or $CH_3$ and $R_4$=H, or n=1, $R_1$=H, $R_2$=$COOC_2H_5$, $R_3$=H or $CH_3$ and $R_4$=H, or n=1, $R_1$=H, $R_2$=$CONHCH_3$, $R_3$=H and $R_4$=H, but including pharmaceutically acceptable acid addition salts of the above-defined compounds of formula (I).

The pyridoindole derivatives are herein referred to for brevity as the "therapeutic compounds".

Preferred therapeutic compounds are those in which $R_1$ is H, Cl, F, $CH_3$, $CH_3O$, $CF_3$ or Br, $R_2$ is $COOCH_3$, $COOC_2H_5$, $CONHCH_3$ or $CONHC_2H_5$, $R_3$ is H, $CH_3$ or $COOC_2H_5$, $R_4$ is H, $CH_3$, $CONH_2$, CONalkyl or $COCH_3$ and n is 0 or 1, subject to the above-mentioned exception clause.

Examples of specifically preferred therapeutic compounds of formula (I) are given in a Table hereinafter and this Table should be construed as extending to the free bases and all pharmaceutically acceptable salts of the free bases.

The invention provides processes for the preparation of the compounds as follows:

1. a process for the preparation of a derivative defined above in which $R_3$ is an alkyl or alkoxycarbonyl radical, which process comprises reacting a compound of the formula

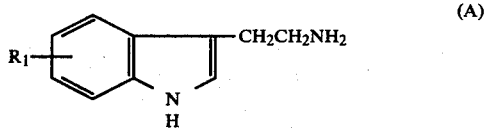
(A)

$R_1$ being as defined above, with a compound of formula $R_3CO(CH_2)_nCOOalkyl$, $R_3$ being as defined above, and the resulting compound (I), in which $R_2$ is COOalkyl and $R_4$ is a hydrogen atom of the formula

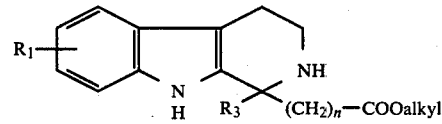
(B)

and if desired this compound is reacted with an amine $R_5NH_2$ to give the compounds (I) in which $R_2$ is $CONHR_5$, and if desired the resultant compound or compound (B) is reacted with an isocyanate $R_6NCO$ to give the compounds (I) in which $R_4$ is $CONHR_6$, $R_6$ being other than a hydrogen atom or with an alkali metal cyanate to give the compounds (I) in which $R_6$ is a hydrogen atom or is N-acylated or N-alkylated by a compound of formula acyl-L or alkyl-L, L representing a leaving group for the reaction, to give the compounds (I) in which $R_4$ is alkyl or acyl, the radicals n, $R_1$, $R_3$, $R_4$, $R_5$ and $R_6$ having the meanings as defined above, and if desired a free base of formula (I) thus obtained is converted into a pharmaceutically acceptable acid addition salt thereof;

2. a process for the preparation of a derivative defined above in which $R_3$ is a hydrogen atom and n is 1, which process comprises reacting a compound of the formula (A')

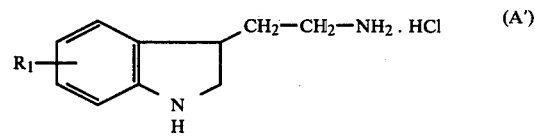
(A')

$R_1$ being as defined above, with the compound EtO—CO—CO—$CH_2$—$COOC_2H_5$, saponifying the resulting diester of formula (B')

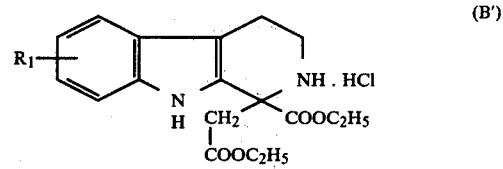
(B')

$R_1$ being as defined above, reacting the resulting diacid with an alcohol of formula alkyl-OH to give a compound (I) in which $R_2$ is COOalkyl and $R_3$ is a hydrogen atom, $R_2$ and $R_3$ being as defined above, and, if desired, reacting this compound in the manner defined for reaction of compound (B) above and if desired a free base of formula (I) thus obtained is converted into a pharmaceutically acceptable acid addition salt thereof;

3. A process for preparing a derivative defined above in which $R_2$ is $CONHR_5$ from a compound defined above in which $R_2$ is an alkoxycarbonyl radical and/or a compound defined above in which $R_4$ is $CONHR_6$, alkyl or acyl from a compound defined above in which $R_4$ is a hydrogen atom, which comprises reacting the said starting compound with an amine $R_5NH_2$, isocyanate $R_6NCO$, $R_6$ being other than a hydrogen atom, alkali metal cyanate or compound of formula acyl-L or alkyl-L, L being a leaving group for the reaction, respectively, $R_5$ and $R_6$ being as defined above and if desired converting a free base of a formula (I) into a pharmaceutically acceptable acid addition salt thereof.

In all the above processes "L" in "alkyl-L" is preferably anion-forming and acyl-L is conveniently a dianhydride of formula (acyl)₂O.

By way of illustration of the processes of the invention, the compounds (I) can be prepared in accordance with the following reaction scheme. "ALK" is alkyl and the other symbols as defined above for formula (I) except where otherwise indicated.

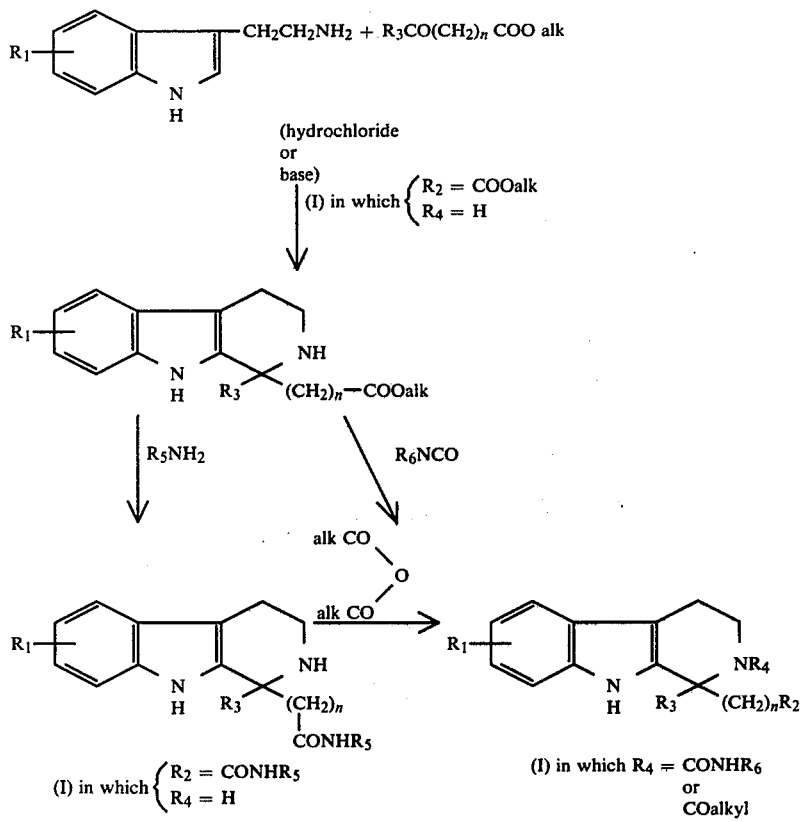

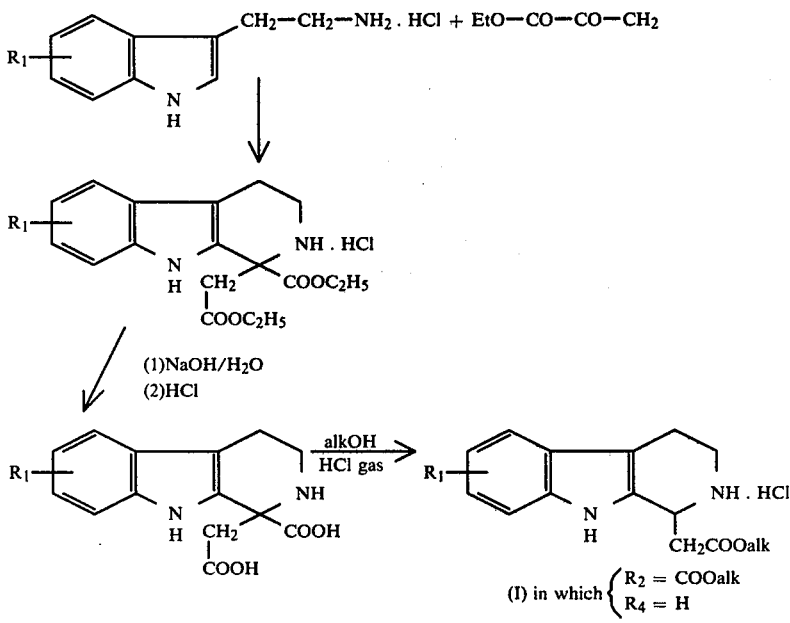

The conversion of the ester (I) into the amide (I) in which $R_2 = CONHR_5$ is effected in the same manner as in reaction scheme 1; likewise, the addition of the radical $R_4$=CONHR$_6$ onto the compounds (I) in which $R_2$=COOalk or CONHR$_5$ is effected in the same manner as in scheme 1.

Alternatively the compounds (I) in which $R_1$ is $CF_3$ or Br can be prepared in accordance with a somewhat different process (see Example 8) adapted from the process described for $R_1$=H in Chem. Abstracts, 60, 5471h.

The compounds in which $R_3$=H and n=0 can be obtained in accordance with the method of preparation described by Z. J. Vejdélek et al., J. of Med. and Pharm. Chem., Volume 3, No. 3 (1961), pages 427–440.

The following examples illustrate the invention. The microanalyses and the IR and NMR spectra confirm the structure of the compounds.

EXAMPLE 1

Ethyl 6-methyl-2,3,4,9-tetrahydro-1H-pyrido[3,4-b]indole-1-acetate

[n=1, $R_1$=6—$CH_3$, $R_2$=COOC$_2$H$_5$, $R_3$=H, $R_4$=H]

1. 52.62 g (0.25 mol) of 5-methyltryptamine hydrochloride are suspended in 250 ml of ethanol and the suspension is heated to the reflux temperature. 57.75 g of 3-ethoxycarbonyl-1,2-dioxo-1-ethoxypropane are suspended in 250 ml of ethanol, and 25 ml of concentrated hydrochloric acid are added dropwise in the course of 10 minutes. The latter suspension is added to the suspension of 5-methyltryptamine HCl, kept at the reflux temperature. The mixture is allowed to cool overnight. The solvent is removed by evaporation, the residue is dissolved in 400 ml of water and the solution is rendered alkaline with ammonia. After extraction with ethyl acetate, an oil is obtained which is chromatographed on a silica column. After elution with an 8/2 mixture of chloroform and ethanol, an oil is obtained which solidifies on trituration with petroleum ether. After recrystallisation from hexane, the compound obtained

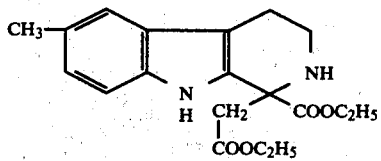

melts at 102°–103° C.

2. 45 g of the preceding compound are heated under reflux in 450 ml of a 10% strength aqueous solution of NaOH for 20 hours. Concentrated hydrochloric acid (100 ml) is added dropwise to the cooled reaction mixture in the course of 30 minutes. The resulting solid is filtered off and dried over $P_2O_5$.

3. 99.6 g of the crude solid obtained above are heated under reflux in a mixture of 250 ml of ethanol and 20 ml of concentrated sulphuric acid for 9 hours. The mixture is left to stand overnight. The ethanol is removed by evaporation and the residual solid is rendered alkaline with ammonia. The basic solution is extracted with 3 times 300 ml of ethyl acetate. The extract is evaporated. An oil is obtained which gives a white solid on trituration with petroleum ether. The solid is filtered off and dried.

After recrystallisation from hexane, the compound obtained melts at 103° C.

EXAMPLE 2

Methyl 6-chloro-1-methyl-2,3,4,9-tetrahydro-1H-pyrido[3,4-b]indole-1-carboxylate

[n=0, $R_1$=6—Cl, $R_2$=COOCH$_3$, $R_3$=CH$_3$, $R_4$=H]

A solution of 36.1 g (0.156 mol) of 5-chlorotryptamine hydrochloride in 350 ml of methanol is reacted with 20 g of methyl pyruvate. The mixture is stirred for one week at ambient temperature. The methanol is driven off on a rotary evaporator. The residue is taken up in ethyl acetate. The mixture is stirred for 15 minutes and the precipitate is then filtered off. The precipitate is treated with a saturated solution of sodium bicarbonate and extraction is carried out with ethyl acetate. An insoluble material is removed by filtration. The organic solution is decanted, washed, dried and evaporated on a water bath in vacuo.

The oily residue crystallises after a few days. After recrystallisation from toluene, the compound melts at 148° C.

EXAMPLE 3

Ethyl 1-methyl-2-methylaminocarbonyl-2,3,4,9-tetrahydro-1H-pyrido[3,4-b]indole-1-acetate

[n=1, $R_1$=H, $R_2$=COOC$_2$H$_5$, $R_3$=CH$_3$, $R_4$=CONHCH$_3$]

10.9 g (0.04 mol) of ethyl 1-methyl-2,3,4,9-tetrahydro-1H-pyrido[3,4-b]indole-1-acetate are suspended in 200 ml of cyclohexane. 3 ml (0.04 mol) of methyl isocyanate are added. The mixture is heated under reflux for 1 hour. It is allowed to cool overnight in a refrigerator. The precipitate is filtered off. The product is recrystallised from ethanol.

Melting point=217° C.

EXAMPLE 4

Ethyl 2-aminocarbonyl-2,3,4,9-tetrahydro-1H-pyrido[3,4-b]indole-1-carboxylate

[n=0, $R_1$=H, $R_2$=COOC$_2$H$_5$, $R_3$=H, $R_4$=CONH$_2$]

56.2 g (0.2 mol) of ethyl 2,3,4,9-tetrahydro-1H-pyrido[3,4-b]indole-1-carboxylate are heated to about 60° C. in 1,000 ml of water. A solution of 15.2 g (0.234 mol) of pulverulent sodium cyanate in 200 ml of water is added all at once. The mixture is stirred for 15 minutes and then cooled to about 10° C. The aqueous reaction phase is decanted and the compound is washed with water and recrystallised from ethanol.

Melting point=215°–217° C.

EXAMPLE 5

1-Methyl-1-methylaminocarbonyl-2,3,4,9-tetrahydro-1H-pyrido[3,4-b]indole

[n=0, $R_1$=H, $R_2$=CONHCH$_3$, $R_3$=CH$_3$, $R_4$=H]

4.8 g (0.02 mol) of methyl 1-methyl-2,3,4,9-tetrahydro-1H-pyrido[3,4-b]indole-1-carboxylate are dissolved in 100 ml of ethanol saturated with methylamine. The solution is left at ambient temperature for 48 hours. The solvent is removed and the residue is then taken up in 20 ml of ethanol. The product is filtered off and washed with ethanol.

Melting point = 230°–231° C.

EXAMPLE 6

6-Fluoro-1-methylaminocarbonyl-2,3,4,9-tetrahydro-1H-pyrido[3,4-b]indole

[n=1, R₁=6-F, R₂=CONHCH₃, R₃=H, R₄=H]

20 g of ethyl 6-fluoro-2,3,4,9-tetrahydro-1H-pyrido[3,4-b]indole-1-acetate (obtained in accordance with the process of Example 1) and 500 ml of ethanol saturated with methylamine are placed in an autoclave. The autoclave is heated at 100° C. for 5 hours. The solvent is driven off and a white solid is obtained. It is recrystallised from ethanol.

Melting point = 227° C.

EXAMPLE 7

6-Chloro-1-methylaminocarbonyl-1-methyl-2-acetyl-2,3,4,9-tetrahydro-1H-pyrido[3,4-b]indole

[n=1, R₁=6-Cl, R₂=CONHCH₃, R₃=CH₃, R₄=COCH₃]

3 g (0.0102 mol) of 6-chloro-1-methylaminocarbonyl-1-methyl-2,3,4,9-tetrahydro-1H-pyrido[3,4-b]indole are dissolved in 30 ml of pyridine. 2 ml of acetic anhydride are added. The mixture is stirred at ambient temperature for 48 hours. It is evaporated and the pyridine is driven off. The residue is taken up in 20 ml of ethanol and the precipitate is filtered off. After recrystallisation from ethanol, the product melts at 214° C.

EXAMPLE 8

Ethyl 6-trifluoromethyl-2,3,4,9-tetrahydro-1H-pyrido[3,4-b]indole-1-acetate

[n=1, R₁=6-CF₃, R₂=COOC₂H₅, R₃=H, R₄=H]

The reaction scheme is as follows:

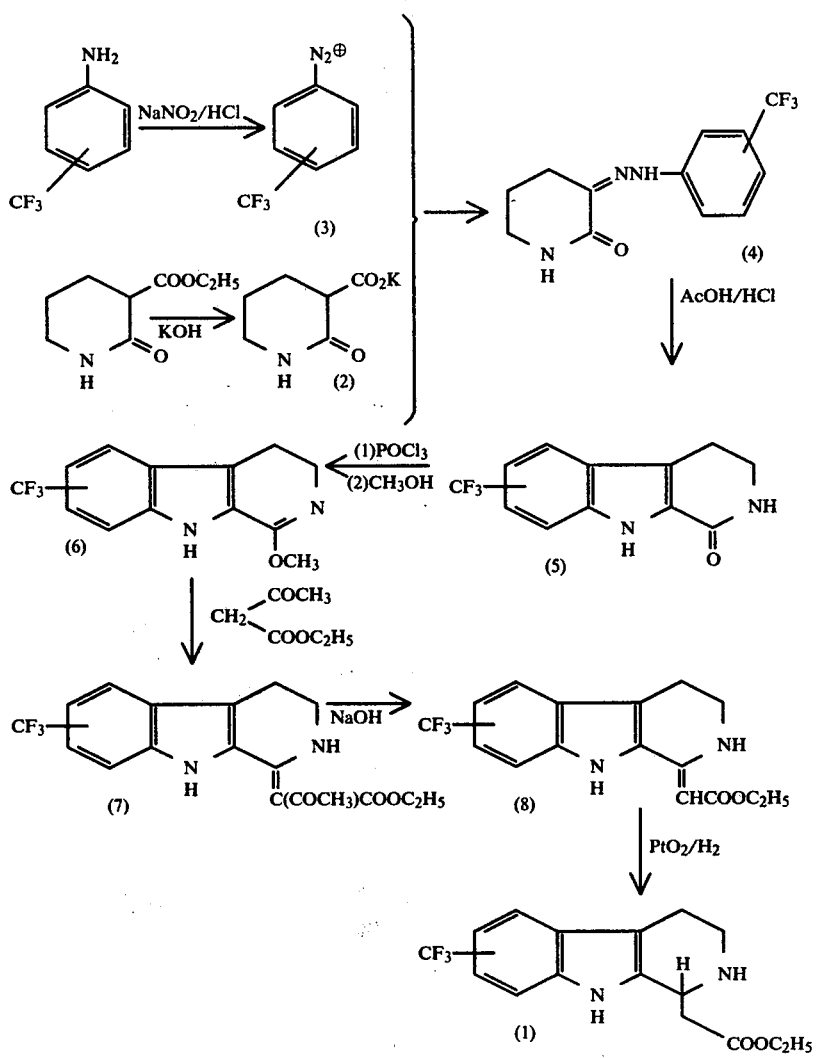

(1) 42.75 g (0.25 mol) of 3-ethoxycarbonylpyrid-2-one are placed in a round-bottomed flask and 500 ml of water are added. 15 g of KOH are added and the mixture is stirred at ambient temperature for 24 hours.

(2) A solution of 4-trifluoromethylaniline (42.25 g) in water (250 ml) and concentrated hydrochloric acid (55 ml) is reacted with 18.75 g of NaNO₂ in 125 ml of water, at a temperature of 0° to 5° C. 50 g of CH₃COONa in 125 ml of water are then added.

(3) The compound obtained under 2 is added, in the course of 10 minutes, at 0°–5° C., to the compound obtained under 1. The mixture is stirred for 5 minutes. 75 ml of acetic acid are added. The mixture is stirred for 4 hours at ambient temperature. The product is filtered off and recrystallised from ethanol.

(4) 30 g of the compound

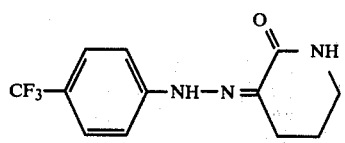

are placed in a round-bottomed flask and 135 ml of glacial acetic acid and 68 ml of hydrochloric acid are added. The mixture is heated at the reflux temperature for 1 hour. The reaction mixture is cooled and poured onto 300 ml of ice. The resulting solid is recrystallised from ethanol.

(5) 15 g of 6-trifluoromethyl-1-oxo-2,3,4,9-tetrahydro-1H-pyrido[3,4-b]indole are placed in a round-bottomed flask and 50 ml of POCl₃ are added. The mixture is stirred at ambient temperature for 24 hours. 60 ml of ethyl ether are added and the product is filtered off. It is washed with 20 ml of ethyl ether and dried in vacuo over P₂O₅ for 2 hours.

60 ml of methanol are placed in a round-bottomed flask and cooled to 0° C. 18.3 g of the compound obtained above are added in portions. The mixture is stirred at ambient temperature for 1 hour. Ethyl ether is added and a precipitate is obtained. After washing the compound, a white product (6) is obtained which melts at 220° C.

(6) 8.5 g of this compound are placed in a round-bottomed flask and 25 ml of ethyl acetoacetate are added. The mixture is heated under nitrogen at 140° C. for 8 hours. The reaction mixture is left to stand overnight. After washing, draining and drying, compound (7) is obtained, which melts at 144° C.

(7) 7.5 g of compound (7) are placed in a round-bottomed flask and 30 ml of ethanol are added. A solution of NaOH (1.25 g) in water (30 ml) is added. The mixture is heated at the reflux temperature for 1 hour. It is cooled in an ice bath. After it has been filtered off and dried in vacuo over P₂O₅, compound (8) melts at 192° C.

(8) 5.2 g of compound (8), 13 ml of acetic acid and 50 ml of ethanol are placed in an autoclave. 0.43 g of platinum oxide is added and the mixture is stirred under hydrogen for 1 and a half hours under pressure. The mixture is filtered and the ethanol is driven off. The residue is rendered alkaline with NH₄OH and the solid is extracted with 4 times 100 ml of ethyl acetate. After drying, an oil is obtained which solidifies. After recrystallisation from ethanol, compound (I) melts at 140° C.

The therapeutic compounds, prepared by way of examples, are shown in the following table.

TABLE

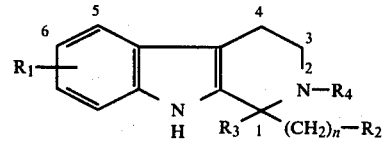

| Compound | R₁ | R₂ | R₃ | R₄ | n | Melting point (°C.) |
|---|---|---|---|---|---|---|
| 1 (Example 1) | 6-CH₃ | COOC₂H₅ | H | H | 1 | 103 |
| 2 | 6-CH₃ | COOC₂H₅ | COOC₂H₅ | H | 1 | 102–103 |
| 3 | 6-CH₃O | COOC₂H₅ | H | H | 1 | 181 (maleate) |
| 4 | 6-CH₃O | COOC₂H₅ | COOC₂H₅ | H | 1 | 100 |
| 5 | H | COOC₂H₅ | COOC₂H₅ | H | 1 | 80–82 |
| 6 | 6-Cl | COOC₂H₅ | CH₃ | H | 1 | 104 |
| 7 | 6-Cl | COOC₂H₅ | H | H | 1 | 240 m.s |
| 8 | 6-Cl | COOC₂H₅ | COOC₂H₅ | H | 1 | 101 |
| 9 | 6-F | COOC₂H₅ | H | H | 1 | 229–230 m.s |
| 10 | 6-F | COOC₂H₅ | COOC₂H₅ | H | 1 | 197 HCl |
| 11 (Example 2) | 6-Cl | COOCH₃ | CH₃ | H | 0 | 148 |
| 12 | H | COOC₂H₅ | H | CONH₂ | 1 | Oil |
| 13 (Example 3) | H | COOC₂H₅ | CH₃ | CONHCH₃ | 1 | 217 |
| 14 (Example 4) | H | COOC₂H₅ | H | CONH₂ | 0 | 215–217 |
| 15 | H | COOC₂H₅ | H | CONHC₂H₅ | 0 | 190–192 |
| 16 | H | COOC₂H₅ | H | CONHC₃H₇—n | 0 | 170–175 |
| 17 | H | COOC₂H₅ | H | CONHC₄H₉—t | 0 | 209–210 |
| 18 | H | COOC₂H₅ | H | CONHCH₃ | 0 | 158–162 |
| 19 | H | COOC₂H₅ | H | CONHC₃H₇—i | 0 | 145–150 |
| 20 | H | COOC₂H₅ | H | CONHC₆H₅ | 0 | 164–168 |
| 21 | H | COOC₂H₅ | H | CONH—⟨⟩—Cl | 0 | 160 |
| 22 | H | COOC₂H₅ | H | CONHC₄H₉—n | 0 | 140 |
| 23 | 6-CF₃ | COOC₂H₅ | H | H | 1 | 140 |
| 24 | 6-Br | COOC₂H₅ | H | H | 1 | Oil |
| 25 | H | COOC₂H₅ | CH₃ | —COCH₃ | 1 | 194 |
| 26 | H | COOCH₃ | CH₃ | COCH₃ | 0 | 238 |
| 27 | H | COOC₂H₅ | H | COCH₃ | 0 | 211–212 |
| 28 | 6-F | COOCH₃ | CH₃ | H | 0 | 248 |
| 29 | 6-CH₃ | COOCH₃ | CH₃ | H | 0 | 142 |
| 30 | H | CONHCH₃ | CH₃ | H | 1 | 182 |
| 31 | 6-Cl | CONHCH₃ | CH₃ | H | 1 | 212 |

TABLE-continued

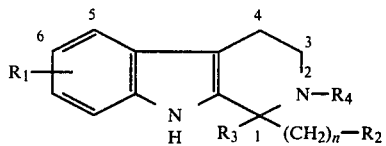

| Compound | R₁ | R₂ | R₃ | R₄ | n | Melting point (°C.) |
|---|---|---|---|---|---|---|
| 32 | H | CONHCH₂—⌬ | H | H | 1 | 160 |
| 33 | H | CONH—▷ | H | H | 1 | 166–168 |
| 34 (Example 6) | 6-F | CONHCH₃ | H | H | 1 | 227 |
| 35 | 6-Cl | CONHCH₃ | H | H | 1 | 232–233 |
| 36 | 6-CH₃ | CONHCH₃ | H | H | 1 | 216 |
| 37 | 6-CH₃O | CONHCH₃ | H | H | 1 | 190 |
| 38 | H | CONHC₂H₅ | H | H | 1 | 148–149 |
| 39 | H | CONHCH₃ | CH₃ | CH₃ | 1 | 240 |
| 40 (Example 5) | H | CONHCH₃ | CH₃ | H | 0 | 230 |
| 41 | H | CONHCH₃ | CH₃ | CH₃ | 0 | 207 |
| 42 | 6-Cl | CONHCH₃ | CH₃ | H | 0 | 230 |
| 43 | 6-F | CONHCH₃ | CH₃ | H | 0 | 238 |
| 44 (Example 7) | 6-Cl | CONHCH₃ | CH₃ | COCH₃ | 1 | 214 |
| 45 | 6-Cl | CONHCH₃ | CH₃ | COCH₃ | 0 | 280 |
| 46 | 6-Cl | CONHC₂H₅ | H | H | 1 | 240 |
| 47 | 6-Cl | CONH—▷ | H | H | 1 | 242 |
| 48 | 6-Cl | CONHCH₃ | CH₃ | COCH₃ | 1 | 214 |
| 49 | 6-Cl | CONHCH₃ | H | COCH₃ | 1 | 267 |
| 50 | H | CONH—⌬—OCH₃ | H | H | 1 | 189 |
| 51 | H | CONHC₂H₅ | CH₃ | H | 0 | 159 |
| 52 | H | CONH—▷ | CH₃ | H | 0 | 164 |
| 53 | 6-Cl | CONHCH₃ | CH₃ | COCH₃ | 0 | 280 |
| 54 | 6-CH₃ | CONHCH₃ | CH₃ | H | 0 | 214 |
| 55 | H | CONHCH₃ | H | H | 0 | 158 |
| 56 | H | CONH₂ | H | H | 1 | 198–200 |
| 57 | H | CONHCH₃ | H | H | 0 | 158 |

HCl = hydrochloride
m.s = methanesulphonate

The therapeutic compounds were subjected to various pharmacological experiments.

In fact, the compounds were subjected to the test for the anoxia caused in mice by pressure reduction and to the test for the antagonism towards the ptosis induced by reserpine (C. Gouret et al., J. Pharmacol. (Paris) 8, 333–350 (1977)).

ANOXIA CAUSED BY PRESSURE REDUCTION

Mice of the CD1 strain are kept in an oxygen-depleted atmosphere produced by creating a partial vacuum (190 mm of mercury, corresponding to 5.25% of oxygen).

The survival time of the animals is noted. This time is increased by agents which are capable of assisting the oxygenation of tissues and in particular of the brain. The compounds studied are administered intraperitoneally in several doses, 10 minutes before the experiment. The percentage increases in the survival time, relative to the values obtained for control animals, are calculated. The mean active dose (MAD), that is to say the dose which increases the survival time by 100%, is determined graphically.

The MAD of the therapeutic compounds varies from 13 to 26 mg/kg, administered intraperitoneally.

ANTI-DEPRESSIVE ACTIVITY

The anti-depressive activity was determined by the test for the antagonism towards the ptosis induced by reserpine (C. Gouret et al., J. Pharmacol. (Paris) 8, 333–350 (1977)).

Mice (male, CD1 Charles River, France, weighing 18–22 g) simultaneously receive the products to be studied or the solvent (administered intraperitoneally) and the reserpine (4 mg/kg, administered subcutaneously).

After sixty minutes, the degree of palpebral ptosis is assessed for each mouse by means of a rating scale (0 to 4).

The mean rating and the percentage variation relative to the control batch are calculated for each dose.

For each product, the $AD_{50}$, namely the dose which reduces the mean ptosis score by 50%, relative to the control animals, is determined graphically.

The $AD_{50}$ varies from 2 to 10 mg/kg, administered intraperitoneally.

ACTION OF THE DURATION OF "SLEEP"

This action was determined by the influence of the compounds on the duration of the "sleep" induced in curarised rats by sodium 4-hydroxybutyrate (GHB); the rats are under artificial respiration and their electrocorticographic activity is recorded by means of cortical electrodes.

The compounds of the invention reduce the total duration of the sleep by 20 to 35%.

The pharmacological study of the therapeutic compounds shows that they are active in the test for the anoxia caused in mice by pressure reduction, whilst being only slightly toxic, and that they exert a significant waking action in the test for the "sleep" induced by sodium 4-hydroxybutyrate.

The therapeutic compounds, which possess both an anti-anoxia action and a psychotropic action, can be used in therapy for the treatment of vigilance disorders, in particular for combating behavioural disorders which can be attributed to cerebral vascular damage and to cerebral sclerosis encountered in geriatrics, and also for the treatment of epileptic vertigo due to cranial traumatisms, and the treatment of depressive states.

The therapeutic compounds can be formulated in pharmaceutical compositions containing the compounds and/or their salts as active principles, in association with any excipients which are suitable for their administration, in particular their oral or parenteral administration.

The methods of administration can be oral and parenteral.

The daily posology can range from 10 to 1,000 mg.

We claim:

1. A compound of the formula

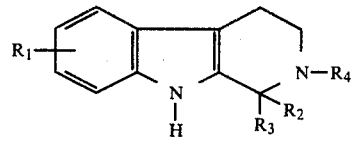

wherein
$R_1$ = H, halogen, $C_{1-4}$ alkyl, $C_{1-4}$ alkoxy, or $CF_3$;
$R_2$ = $CONHR_5$ in which $R_5$ is $C_{1-4}$ alkyl, $C_{3-6}$ cycloalkyl or benzyl;
$R_3$ = H or $CH_3$; and
$R_4$ = H, $CH_3$ or $CH_3CO$;
or a pharmaceutically acceptable salt thereof.

2. A compound as claimed in claim 1, where said compound is 1-methyl-1-methylaminocarbonyl-2, 3, 4, 9-tetrahydro-1H-pyrido [3,4,-b] indole, or a pharmaceutically acceptable salt thereof.

3. A pharmaceutical composition comprising a compound as claimed in claim 1 in association with a pharmaceutically acceptable excipient.

4. A method of treating a patient for anoxia, comprising administering to the patient a therapeutically effective dose of a compound as claimed in claim 1.

* * * * *